(12) United States Patent  (10) Patent No.: US 9,176,065 B2
Bond et al.  (45) Date of Patent: Nov. 3, 2015

(54) NANOSCALE ARRAY STRUCTURES SUITABLE FOR SURFACE ENHANCED RAMAN SCATTERING AND METHODS RELATED THERETO

(71) Applicants: LAWRENCE LIVERMORE NATIONAL SECURITY, LLC, Livermore, CA (US); THE BOARD OF TRUSTEES OF THE UNIVERSITY OF ILLINOIS, Urbana, IL (US)

(72) Inventors: Tiziana C. Bond, Livermore, CA (US); Robin Miles, Danville, CA (US); James C. Davidson, Livermore, CA (US); Gang Logan Liu, Champaign, IL (US)

(73) Assignees: Lawrence Livermore National Security, LLC, Livermore, CA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/316,024

(22) Filed: Jun. 26, 2014

(65) Prior Publication Data

US 2014/0333926 A1  Nov. 13, 2014

Related U.S. Application Data

(63) Continuation of application No. 12/957,883, filed on Dec. 1, 2010, now Pat. No. 8,786,852.

(60) Provisional application No. 61/266,036, filed on Dec. 2, 2009.

(51) Int. Cl.
*G01J 3/44* (2006.01)
*G01N 21/65* (2006.01)
(Continued)

(52) U.S. Cl.
CPC .......... *G01N 21/658* (2013.01); *B81C 1/00373* (2013.01); *B82Y 20/00* (2013.01); *G01N 21/01* (2013.01); *B82Y 15/00* (2013.01)

(58) Field of Classification Search
CPC ....... G01N 21/64; G01N 21/65; G01N 21/68; G01N 21/658; G01N 2021/656; G01J 3/02; G01J 3/44
USPC ............................................. 356/301, 72–73
See application file for complete search history.

(56) References Cited

U.S. PATENT DOCUMENTS 5,401,897 A  3/1995 Depalle et al.
5,485,277 A  1/1996 Foster
(Continued)

FOREIGN PATENT DOCUMENTS

FR  2679689  1/1993
FR  2782228  2/2000
(Continued)

OTHER PUBLICATIONS

Non-Final Office Action mailed on Sep. 2, 2014 for U.S. Appl. No. 14/302,276, filed Jun. 11, 2014 in the name of Tizia C. Bond et al.
(Continued)

*Primary Examiner* — Abdullahi Nur
(74) *Attorney, Agent, or Firm* — Steinfl & Bruno LLP (57) ABSTRACT

Methods for fabricating nanoscale array structures suitable for surface enhanced Raman scattering, structures thus obtained, and methods to characterize the nanoscale array structures suitable for surface enhanced Raman scattering. Nanoscale array structures may comprise nanotrees, nanorecesses and tapered nanopillars.

30 Claims, 10 Drawing Sheets

(51) Int. Cl.
*B82Y 20/00* (2011.01)
*G01N 21/01* (2006.01)
*B81C 1/00* (2006.01)
*B82Y 15/00* (2011.01)

(56) References Cited

U.S. PATENT DOCUMENTS

| | | | |
|---|---|---|---|
| 5,496,701 | A | 3/1996 | Pollard-Knight |
| 5,500,900 | A | 3/1996 | Chen et al. |
| 5,596,644 | A | 1/1997 | Abel et al. |
| 5,832,165 | A | 11/1998 | Reichert et al. |
| 5,843,767 | A | 12/1998 | Beattie |
| 6,023,540 | A | 2/2000 | Walt et al. |
| 6,146,767 | A | 11/2000 | Schwartz |
| 6,356,676 | B1 | 3/2002 | Herron et al. |
| 6,611,634 | B2 | 8/2003 | Herron et al. |
| 6,785,732 | B1 | 8/2004 | Bates et al. |
| 6,801,677 | B1 | 10/2004 | Grace et al. |
| 6,829,073 | B1 | 12/2004 | Krol et al. |
| 7,155,076 | B2 | 12/2006 | Letant et al. |
| 7,318,907 | B2 | 1/2008 | Stark et al. |
| 7,351,588 | B2 | 4/2008 | Poponin |
| 7,476,787 | B2 * | 1/2009 | Thomas et al. ............... 250/306 |
| 7,713,849 | B2 | 5/2010 | Habib et al. |
| 8,059,824 | B2 | 11/2011 | Pallone et al. |
| 8,059,924 | B1 | 11/2011 | Letant et al. |
| 8,427,639 | B2 | 4/2013 | Moskovits et al. |
| 8,780,439 | B2 | 7/2014 | Bora et al. |
| 8,947,657 | B2 | 2/2015 | Letant et al. |
| 9,080,981 | B2 | 7/2015 | Bond et al. |
| 2003/0133639 | A1 | 7/2003 | Tao et al. |
| 2004/0023396 | A1 | 2/2004 | Boyd et al. |
| 2005/0078903 | A1 | 4/2005 | Grace et al. |
| 2005/0135723 | A1 | 6/2005 | Carr et al. |
| 2006/0085200 | A1 | 4/2006 | Allamanche et al. |
| 2007/0160216 | A1 | 7/2007 | Nicol et al. |
| 2008/0008323 | A1 | 1/2008 | Hilpert et al. |
| 2008/0094621 | A1 * | 4/2008 | Li et al. ............... 356/301 |
| 2008/0174775 | A1 | 7/2008 | Moskovits |
| 2010/0177903 | A1 | 7/2010 | Vinton et al. |
| 2011/0075848 | A1 | 3/2011 | Purnhagen et al. |
| 2011/0128536 | A1 | 6/2011 | Bond et al. |
| 2011/0166045 | A1 | 7/2011 | Dhawan et al. |
| 2012/0081703 | A1 | 4/2012 | Moskovits et al. |

FOREIGN PATENT DOCUMENTS

| | | |
|---|---|---|
| FR | 2851879 | 9/2004 |
| WO | 01/36945 | 5/2001 |
| WO | 2005/069272 | 7/2005 |
| WO | 2007/104877 | 9/2007 |

OTHER PUBLICATIONS

Notice of Allowance mailed on May 5, 2014 for U.S. Appl. No. 12/958,302, filed Dec. 1, 2010 in the name of Tiziana C. Bond et al.
Final Office Action mailed on Jun. 19, 2014 for U.S. Appl. No. 13/117,079, filed May 26, 2011 in the name of Sonia Edith Letant et al.
Notice of Allowance mailed on Oct. 7, 2014 for U.S. Appl. No. 13/117,079, filed May 26, 2011 in the name of Sonia Edith Letant et al.
Non-Final Office Action mailed on Nov. 27, 2013 for U.S. Appl. No. 13/410,226, filed Mar. 1, 2012 in the name of Mihail Bora et al.
Notice of Allowance mailed Mar. 17, 2014 for U.S. Appl. No. 13/410,226, filed Mar. 1, 2012 in the name of Mihail Bora et al.
Hirsch, L. R.; Jackson, J. B.; Lee, A.; Halas, N. J.; West, J., "A Whole Blood Immunoassay Using Gold Nanoshells", Analytical Chemistry 2003, 75, 2377-2381.
Rich, R. L.; Myszka, D. G., "Advances in surface plasmon resonance biosensor analysis", Current Opinion in Biotechnology 200, 11, 54-61.

Bora, M.; Celebi, K.; Zuniga, J.; Watson, C.; Milaninia, K. M.; Baldo, M. A., "Near field detector for integrated surface plasmon resonance biosensor applications", Optics Express 2009, 17, 329-336.
Barnes, W. L.; Dereux, A.; Ebbesen, T. W., "Surface plasmon subwavelength optics", Nature 2003, 424, 824-830.
Ghaemi, H. F.; Thio, T.; Grupp, D. E.; Ebbesen, T. W.; Lezec, H. J., "Surface plasmons enhance optical transmission through subwavelength holes", Physical Review B 1998, 58, 6779-6782.
Lezec, H. J.; Degiron, A.; Devaux, E.; Linke, R. A.; Martin-Moreno, L.; Garcia-Vidal, F. J.; Ebbesen, T. W., "Beaming Light from a Subwavelength Aperature", Science 2002, 297, 820-822.
Morfa, A. J.; Rowlen, K. L.; Reilly, T. H.; Tenent, R.C.; van de Lagemaat, J., "Surface-plasmon enhanced transparent electrodes in organic photovoltaics", Applied Physics Letters 2008, 92, 243304-1-243304-3.
Tvingstedt, K.; Persson, N. K.; Inganas, O.; Rahachou, A.; Zozoulenko, I. V., "Surface plasmon Increase absorption in polymer photovoltaic cells", Applied Physics Letters 2007, 91, 113514-1-113514-3.
Westphalen, M.; Kreibig, U.; Rostalski, J.; Luth, H.; Meissner, D., "Metal cluster enhanced organic solar cells", Solar Energy Materials and Solar Cells 2000, 61, 97-105.
Miyazaki, H. T.; Kurokawa, Y., "Controlled plasmon resonance in closed metal/insulator/metal nanocavities", Applied Physics Letters 2006, 89, 211126-1-21126-3.
Haynes, C. L.; Van Duyne, R. P., "Nanosphere Lithography: A Versatile Nanofabrication Tool for Studies of Size-Dependent Nanoparticle Optics", Journal of Physical Chemistry B 2001, 105, 5599-5611.
Haynes, C. L.; Van Duyne, R. P., "Plasmon-Sampled Surface-Enhanced Raman Excitation Spectroscopy", Journal of Physical Chemistry B 2003, 107, 7426-7433.
Michaels, A. M.; Nirmal, M.; Brus, L. E., "Surface-Enhanced Raman Spectroscopy of Individual Rhodamine 6G Molecules on Large Ag Nanocrystals", Journal of the American Chemical Society 1999, 121, 9932-9939.
Noginov, M.; Zhu, G.; Belgrave, A.; Bakker, R.; Shaleev, V.; Narimanov, E.; Stout, S.; Herz, E.; Suteewong, T.; Wiesner, U., "Demonstration of a spaser-based nanolaser", Nature 2009, 460, 1110-1113.
Zhang, S.; Berguiga, L.; Elezgaray, J.; Roland, T.; Faivre-Moskalenko, C.; Argoul, F., "Surface plasmon resonance characterization of thermally evaporated thin gold films", Surf. Sci. 2007, 601, 5445-5458.
Manjavacas, A.; de Abajo, F. J. G., "Robust Plasmon Waveguides in Strongly Interacting Nanowire Arrays", Nano Letters 2009, 9, 1285-1289.
Manjavacas, A.; de Abajo, F. J. G., "Coupling of gap plasmons in multi-wire waveguides", Optics Express 2009, 17, 19401-19413.
Stegeman, G. I.; Wallis, R. F.; Maradudin, A. A., "Excitation of surface polaritons by end-fire coupling", Optics Letters 1983, 8, 386-388.
Fernandez, A.; Nguyen, H. T.; Britten, J. A.; Boyd, R. D.; Perry, M. D.; Kania, D. R.; Hawryluk, A. M., "Use of interference lithography to pattern arrays of submicron resist structures for a field emission flat panel displays", Journal of Vacuum Science & Technology B 1997, 15, 729-735.
Dionne, J. A.; Sweatlock, L. A.; Atwater, H. A.; Polman, A., "Plasmon slot waveguides: Towards chip-scale propagation with sub-wavelength scale localization", Physical Review B 2006, 73, 035407, 1-9.
Lezec, H. J.; Dionne, J. A.; Atwater, H. A., "Negative Refraction at Visible Frequencies", Science 2007, 316, 430-432.
Prodan, E.; Radloff, C.; Halas, N. J.; Norlander, P., "A Hybridization Model for the Plasmon Response of Complex Nanostructures", Science 2003, 302, 419-422.
Sun, Z. J.; Zeng, D. Y., "Coupling of Surface Plasmon Waves in Metal/Dielectric Gap Waveguides and Single Interface Waveguides", Journal of the Optical Society of America B-Optical Physics 2007, 24, 2883-2887.
Johnson, P. B.; Christy, R. W., "Optical Constants of the Noble Metals", Physical Review B 1972, 6, 4370-4379.

(56) References Cited

OTHER PUBLICATIONS

Notice of Allowance mailed Mar. 4, 2004 for U.S. Appl. No. 10/159,175, filed May 31, 2002 in the name of Sonia Letant et al.
Non-Final Office Action mailed on Apr. 14, 2006 for U.S. Appl. No. 10/833,573, filed Apr. 27, 2004 in the name of Sonia Letant et al.
Final Office Action mailed on Mar. 9, 2006 for U.S. Appl. No. 10/833,573, filed Apr. 27, 2004 in the name of Sonia Letant et al.
Non-Final Office Action mailed on Sep. 29, 2005 for U.S. Appl. No. 10/833,573, filed Apr. 27, 2004 in the name of Sonia Letant et al.
Notice of Allowance mailed on Jul. 26, 2006 for U.S. Appl. No. 10/833,573, filed Apr. 27, 2004 in the name of Sonia Letant et al.
International Search Report mailed on Aug. 7, 2007 for International Patent Application No. PCT/FR2007/050868 filed on Mar. 1, 2007 (English Translation + French Original).
Written Opinion mailed on Aug. 7, 2007 for International Patent Application No. PCT/FR2007/050868 filed on Mar. 1, 2007.
International Preliminary Report on Patentability completed on Dec. 3, 2008 for International Patent Application No. PCT/FR2007/050868 filed on Mar. 1, 2007.
Lee, M.R. et al. "Two-dimensional silicon photonic crystal based biosensing platform for protein detection." Optics Express, 15(8), pp. 4530-4535, 2007.
Sherry, L. et al, "Localized Surface Plasmon Resonance Spectroscopy of Single Silver Nanocubes." Nano. Lett. 2005, 5(10), pp. 2034-2038.
Canham, L.T. "Silicon quantum wire array fabrication by electrochemical and chemical dissolution of wafers." Appl. Phys. Lett., vol. 57, 1990, pp. 1046-1048.
Lehmann, V. et al. "Formation Mechanism and Properties of Electrochemically Etched Trenches in n-Type Silicon," J. Electrochem. Soc. vol. 137(2), pp. 653-659, 1990.
Birner, A. et al. "Silicon-Based Photonic Crystals." Adv. Mat. vol. 13(6), pp. 377-388, 2001.
Foresi, J.S. et al. "Photonic-bandgap microcavities in optical waveguides." Nature vol. 390, pp. 143-145, 1997.
Hsu, F. et al. "Growth of High-Density Titanium Silicide Nanowires in a Single Direction on a Silicon Surface." Nano Letters, vol. 7(4), pp. 885-889, 2007.
Magagnin, L. et al. "Gold deposition by Galvanic Displacement on Semiconductor Surface: Effect of Substrate on Adhesion." J. Phys. Chem. B. 106. pp. 401-407, 2002.
Segalman, R.A. "Patterning with block copolymer thin films." Mat. Sci. and Eng. R. 48, pp. 191-226. 2005.
Fitz, J.L. et al., "Integrated Photonic Inverter with Gain." IEEE PTL. vol. 13(5), pp. 478-480, May 2001.
Vercoutere, W. et al. "Rapid discrimination among individual DNA hairpin molecules at single-nucleotide resolution using an ion channel." Nature Biotechnology, vol. 19, pp. 248-252, Mar. 2001.
Jirage, K. et al. "Nanotube-based Molecular-Filtration Membranes." Science, vol. 278, pp. 655-658, 1997.
Birner, A. et al. "Transmission of microactivity structure in a two-dimensional photonic crystal based on macroporous silicon" Materials Science in Semiconductor Processing 3, pp. 487-491 2000.
Blanco, A. et al."Large-scale synthesis of a silicon photonic crystal with a complete three dimensional bandgap near 1.5 micrometer." Nature 405, pp. 437-440, 2000.
Lehmann, V. "The Physics of Macropore Formation in Low Doped n-Type Silicon." J. Electrochem. Soc. 140(10), pp. 2836-2843, 1993.
Sigalas, M. et al. "Photonic band gaps and defects in two dimensions: studies of the transmission coefficient." Phys. Rev. B 48(19), pp. 14121-14126 (1993).
McCall, S.L. et al. in "Microwave propagation in two-dimensional dielectric lattices." Phys. Rev. Lett. vol. 67(15), pp. 2017-2020 (1991).
Janshoff, A. et al. "Macroporous p-type silicon Fabry-Perot layers. Fabrication, characterization, and applications in biosensing," J. Am. Chem. Soc. 120. pp. 12108-12116 (1998).
Buriak, J.M. et al. "Lewis acid mediated hydrosilylation on porous silicon." J. Am. Chem. Soc. 121, pp. 11491-11502 (1999).
Dancil, K.P. et al, "A Porous Silicon Optical Biosensor: Detection of Reversible Binding of IgG to a Protein A-Modified Surface," J. Am. Chem. Soc. 121, pp. 7925-7930, 1999.
Boukherroub, R. et al. In "Thermal hydrosilylation of undecylenic acid with porous silicon", Journal of The Electrochemical Society, vol. 149(2). H59-H63 (2002).
Smith, III, J.O., "Viewpoints on the History of Digital Synthesis." Proceedings of the International Computer Music Conference (ICMC-91, Montreal), pp. 1-14, Dec. 28, 2005.
denBrinker, A.C., et al. "Parametric coding for High-Quality Audio" 112th AES convention, Munich, Germany. 10 pgs. May 10-13, 2002.
Szczerba, M., et al. "Parametric Audio Coding Based Wavetable Synthesis." 116th AES convention, Berlin, Germany, 6 pgs. May 8-11, 2004.
Daniel, J. "Spatial Sound Encoding Including Near Field Effect: Introducing Distance Coding Filters and a Viable, New Ambisonic Format." AES 23$^{rd}$ International Conference, Copenhagen, Denmark: 15 pgs. May 23-25, 2003.
Pallone, G. Dilatation et transposition sous contraintes perceptives des signaux audio: Application au transfert cinema-diso. 250 pgs. 2003.
Notice of Allowance mailed on Sep. 12, 2011 for U.S. Appl. No. 12/225,097, filed Oct. 24, 2008 in the name of Gregory Pallone et al.
Non-Final Office Action issued for U.S. Appl. No. 14/302,276, filed Jun. 11, 2014 in the name of Tiziana C. Bond et al. Mail Date: Dec. 4, 2014.
Notice of Allowance issued for U.S. Appl. No. 14/302,276, filed Jun. 11, 2014 in the name of Tiziana C. Bond et al. Mail Date: Mar. 16, 2015.

\* cited by examiner

NANOSCALE ARRAY STRUCTURES SUITABLE FOR SURFACE ENHANCED RAMAN SCATTERING AND METHODS RELATED THERETO

CROSS REFERENCE TO RELATED APPLICATIONS

The present application is a US Continuation application of Ser. No. 12/957,883, filed on Dec. 1, 2010, and incorporated herein by reference in its entirety, which, in turn, claims priority to U.S. Provisional Application No. 61/266,036, filed on Dec. 2, 2009, which is incorporated herein by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to microstructures and their fabrication methods. In particular, it relates to array structures suitable for surface enhanced Raman scattering and methods related thereto.

BACKGROUND

Raman scattered light is considered a chemical signature of chemical and biological molecules since all molecules with unique chemical compositions have unique Raman scattering spectra. Raman scattering spectroscopy is thus a powerful technique to detect chemical and biological molecules without labeling and has potential applications in high-sensitivity detections of explosives, pathogens, and contaminants in the field. Unfortunately, Raman scattering is an extremely inefficient process due to its weak sensitivity as compared to other scattering mechanisms (roughly only 1 in $10^8$ photons ends up in Raman scattering) [Jarvis and Goodacre, 2004 *Anal. Chem.* 76 40] and also due to typical lower scattering cross-sections of Raman process ($\sim 10^{-30}$ cm$^2$), which is around 15 orders of magnitude lower than fluorescence emission [Vo-Dinh et al., 2002 *J. Raman Spectrosc.* 33 511]. In order to get detectable Raman scattering, it is necessary to use an array of filtering techniques or to enhance the Raman scattering process. The latter of the two can be achieved using surface enhanced Raman scattering, which is also known as surface enhanced Raman scattering spectroscopy or surface enhanced Raman spectroscopy. For the sake of clarity, throughout the present disclosure, the term "SERS" intends to indicate surface enhanced Raman scattering.

Back in the 1970's, many scientists came to discover a new phenomenon in Raman scattering, which is now widely referred to as SERS. When chemical and bio-molecules are adsorbed on a roughened noble metal surface, the Raman scattering light can be enormously amplified and the sensitivity of the Raman spectroscopy enhanced by several orders of magnitude. One of the many approaches that has been tried includes microscale or nanoscale "roughening," such as in the form of electrochemical texturing of a surface before metal sputtering [Murray et al., 1981 *Phys. Rev. Lett.* 46 57]. In general, reported signal enhancements have been significant. However, enhancement is observed only at so-called "hot spots," regions where the Raman signal is higher, while neighboring regions might exhibit little or even no significant signal enhancement.

For the sake of clarity, throughout the present disclosure, the term "hot spot", "hot spots", or "SERS hot spots" intends to indicate regions where the Raman signal is higher, or enhanced. The low concentration of hot spots within a sample is exacerbated further by an inconsistency of performance between different but essentially identical substrates, or sample-to-sample uniformity [Netti et al., 2005 *Raman Technology for Today's Spectroscopists*]. Overall, these two aspects together effectively have prevented SERS from being widely recognized as a quantifiable spectroscopic technique [Etchegoin and Le Ru, 2008 *Phys. Chem. Chem. Phys.* 10 6079-6089].

SUMMARY

According to a first aspect, a structure is provided, comprising: a planar substrate; an array of nanopillars on the planar substrate, the array of nanopillars substantially perpendicular to the planar substrate and having a substantially cylindrical shape; a metal drop having a substantially spherical shape on each nanopillar of the array of nanopillars; and a second metal covering a surface of the planar substrate.

According to a second aspect, a structure is provided, comprising: a planar substrate; an array of nanorecesses in the planar substrate; and a first metal covering the planar substrate and the array of nanorecesses.

According to a third aspect, a structure is provided, comprising: a planar substrate; an array of tapered nanopillars on the planar substrate, wherein each tapered nanopillar of the array of tapered nanopillars is substantially perpendicular to the planar substrate and have a substantially conical shape, the conical shape being wider on a side connected with the planar substrate and tapered on a side opposite the planar substrate; and a metal layer covering a surface of the planar substrate and covering each tapered nanopillar of the array of tapered nanopillars.

According to a fourth aspect, a structure is provided, comprising: a planar substrate; an array of straight nanopillars on the planar substrate, wherein each straight nanopillar of the array of straight nanopillars is substantially perpendicular to the planar substrate and have a substantially cylindrical shape; and a metal layer covering a surface of the planar substrate and covering each straight nanopillar of the array of straight nanopillars.

According to a fifth aspect, a method for fabricating a structure is provided, the method comprising: providing a planar substrate; coating the planar substrate with a polymer layer; annealing the polymer layer, wherein the annealing causes a microphase separation of the polymer layer into first portions and second portions, the first portions being an array of nanostructures surrounded by the second portions, the second portions being a polymer matrix; removing the array of nanostructures, whereby the removing forms an array of nanorecesses and the removing exposes portions of the planar substrate below the removed nanostructures; and coating a first metal on the polymer matrix and the exposed portions of the planar substrate.

According to a sixth aspect, a method for fabricating a structure is provided, the method comprising: providing a planar substrate; coating a photoresist layer on the planar substrate; exposing the photoresist layer with laser light, the laser light forming a spatial interference pattern on the photoresist layer; developing the photoresist layer to form an array of photoresist islands according to the spatial interference pattern; removing portions of the planar substrate not covered by the array of photoresist islands, wherein the removing forms an array of tapered nanopillars on the planar substrate; removing the array of photoresist islands; and coating a metal layer on the array of tapered nanopillars.

According to a seventh aspect, a method for measuring a light enhancement factor for an array structure in surface enhanced Raman scattering is provided, the method comprising: providing the structure according to the first aspect; contacting a plurality of molecules with the structure, the plurality of molecules being on the metal drop and on the second metal; and measuring a near field scattering intensity from the structure with a near field scanning optical microscope, thus measuring the light enhancement factor for the structure in surface enhanced Raman scattering (SERS).

According to an eighth aspect, a method for measuring a local electric field intensity with nanometer resolution for an array structure in surface enhanced Raman scattering, the method comprising: providing the structure according to the first aspect; placing a plurality of semiconductor quantum dots or artificial fluorophore molecules in a plurality of hot spots in the structure; and measuring a photoluminescence and/or a fluorescence spectroscopy and calculating the expected local electric field intensity based on quantum-confined Stark effect, thus measuring the local electric field intensity with nanometer resolution for the structure.

Further embodiments of the present disclosure can be found in the written specification, drawings and claims of the present application. According to some embodiments of the present disclosure, the teachings of the present disclosure provide methods for fabricating nanoscale array structures suitable for surface enhanced Raman scattering, structures thus obtained, and methods to characterize the nanoscale array structures suitable for surface enhanced Raman scattering.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 1A-1J show fabrication steps of a structure in accordance with an embodiment of the present disclosure. In particular:

FIGS. 2A-2I show fabrication steps of a structure in accordance with another embodiment of the present disclosure. In particular:

DETAILED DESCRIPTION

The applicants disclose methods to create array structures suitable for SERS which addresses the two known limitations of SERS substrates according to current art: the low concentration of "hot spots" where significant signal enhancement is seen, and the consistency and uniformity of performance from sample to sample. The applicants disclose the application of highly uniform batch nano-fabrication methods: block copolymer nano-lithography and laser interference lithography to fabricate uniform nano scale patterns on wafer size samples, as well as the subsequent processing to create highly uniform nanoscale plasmonic antenna array structures suitable for SERS with high concentration of hot spots. The applicants also disclose methods to characterize the array structures suitable for SERS, confirming significant improvement in the local electric field intensity, the concentration of hot spots and the consistency of performance over current art by measuring the enhancement factor and its repeatability.

Figure 4:
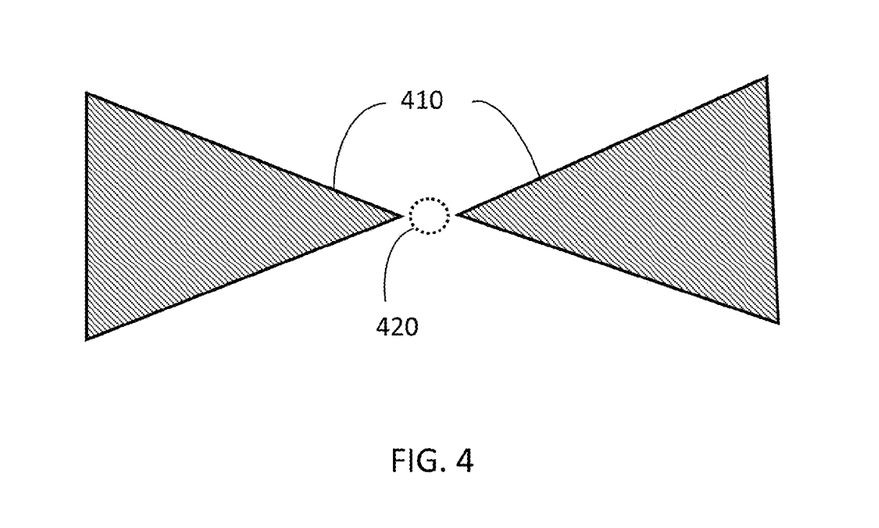
FIG. 4 shows an exemplary plasmon nano-capacitor structure.

First, the applicants disclose the design of a plurality of nanoscale plasmonic antenna array structures suitable for SERS. Plasmons describe the collective free electron oscillations in metallic nanostructures upon excitation by external electromagnetic field. That is, the free electrons in metal may be driven by optical excitations and, at the plasmon resonance frequency, the free electron oscillation can maintain the highest kinetic energy level. If the applicants carefully design a nanoscale plasmonic antenna array to "squeeze" most of the free electrons to an extremely small area and bring two such areas very close to each other, the applicants can artificially make a plasmon nanocapacitor structure (410) as illustrated in FIG. 4 with a hot spot (420) in the center formed by the two triangles shown in FIG. 4. In practice, the hot spot (420) of the nanocapacitor structure (410) may not have to be formed by two triangular shapes but may be formed by two curved surfaces or two flat surfaces with pointed or curved features that are close to each other.

Figure 5:
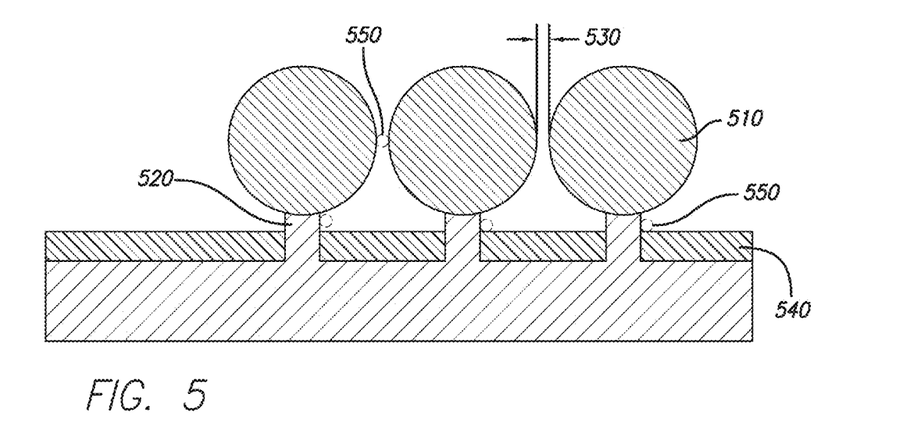
FIG. 5 shows an exemplary detailed view of an array structure suitable for SERS.

By mimicking the structure of a tree and forest, applicants create arrays of metal topped nanopillars such as nanotrees and nanoforest to act like optical antennas that can collect far field optical excitation, generate both localized and surface resonant plasmons, and create SERS hot spots for SERS. The term "hot spots" have previously been defined in the Background Section of the present disclosure as locations where Raman signal enhancement is expected. The illustration of individual nanotrees is depicted in FIG. 5. The nanotree (510) can be a substantially spherical or hemispherical metal drop on the nanotrunk, which can be a short silicon nanopillar (520) as shown in FIG. 5. The nanotrees can be arranged side by side with a gap width (530) of about 50 nm or less from each other to form a high-density array of nanotrees or nanoforest. A gap width of about or less than 10 nm is preferable for SERS. The ground substrate underneath the nanoforest can be covered with a metal thin film (540). In the present disclosure, the applicants also disclose a structure comprising an array of metal covered tapered pillars, a structure comprising metal covered straight pillars, and yet another structure comprising an array of metal covered nanodimples or nanorecesses.

For the sake of clarity, throughout the present disclosure, the term "SERS substrate" intends to indicate any substrate onto which surface enhanced Raman scattering occurs when molecules are contacted to the substrate. The nanoscale array structures disclosed in the present disclosure are all suitable for SERS and therefore each nanoscale array structure can be a SERS substrate. Also for the sake of clarity, throughout the present disclosure, the term "hot spot", "hot spots", or "SERS hot spots" intends to indicate regions where the Raman signal is higher, or enhanced, as previously stated in the Background Section of the present disclosure.

The applicants note that these three-dimensional (3D) arrayed nanodevices serve as excellent SERS substrates due to the following advantages. First, the gaps between adjacent substantially spherical metal nanotrees (510) are potential SERS hot spots (550), which resemble the typical SERS hot spots created in aggregated nanoparticle clusters in current art while maintaining a higher uniformity and order than in current art. Second, the rims of the metal covered arrays of nanorecesses can also serve as the SERS hot spots which resemble the current art of nano-ring devices [Aizpurua et al., 2003 *Phys. Rev. Lett.* 90 057401-057404]. Third, the gaps between the nanotrees (510) and the metal thin film (540) on the ground substrate can be SERS hot spots (550) also, due to the inter-coupling of the localized plasmon in the nanotree (510) and the surface plasmon on the metal thin film (540) covering the substrate. Lastly, the plasmon resonance of the proposed array of nanotrees may be much stronger than that of individual nanotrees or randomly ordered array of nanostructure due to coupling.

The nanoscale array structures suitable for SERS of the present disclosure also have the additional advantage of being tunable. The structures can be tuned by varying, for example, gap width, height of pillars, or use of dielectric fill materials of various refractive indexes in the gaps, the details of which is discussed in Bora et al., 2010 *Nano Lett.* 10 2832-2837 the content of which is incorporated herein by reference in its entirety [Bora et al., 2010 *Nano Lett.* 10 2832-2837]. The pitch (e.g., distance from the center of the nanotree (510) to the center of the next nanotree (510)) of the structures can also be changed by, for example, the use of lasers with different characteristic wavelengths during laser interference lithography.

Furthermore, the 3D nanoscale array structures of the present disclosure can also be used in other applications besides SERS. Possible applications, by way of example and not of limitation, include solar cells, energy harvesting devices, plasmonic nanolasers, tunable sources, supercapacitors and batteries, as well as plasmonic based chemical and biosensors.

The applicants note that the nanotree of the present disclosure can be a plasmon photonic crystal whose plasmon resonance frequency and strength are dependent on not only the individual nanoparticle but also the interparticle coupling. The metal thin film on the substrate can be also a classic plasmon photonic crystal structure with the plasmon resonance frequency and strength dependent on the gap width. This 3D plasmon photonic crystal structure can permit sharper and stronger plasmon resonance with less inhomogeneous broadening and energy damping. Furthermore, the 3D array of nanotrees can contain higher density of hot spots per unit area than any previously demonstrated SERS substrate devices. In practical applications, molecules can have higher possibility to be at the position of the SERS hot spots due to the higher density of hot spots.

In the present disclosure, the applicants describe several large-area highly uniform tunable nanoscale array structures suitable for SERS and methods of fabricating the array structures. Also described in the present disclosure is the result of optical characterization, which verifies an exemplary embodiment of a tapered nanopillar array structure suitable for SERS by quantifying the Raman enhancement factor, uniformity and repeatability. An average homogeneous enhancement factor of well into the $10^7$ range was obtained for an exemplary embodiment of benzenethiol molecules adsorbed on the tapered nanopillar array structure substrate [Garda et al., 2010 Nanotechnology 21 395701-395709]. In what follows, array structures suitable for surface enhanced Raman scattering, fabrication methods thereof, and characterization methods thereof are described in accordance with various embodiments of the present disclosure.

FIGS. 1A-1J show one embodiment of the steps of fabricating an array structure suitable for SERS in accordance with the present disclosure.

Figure 1A:
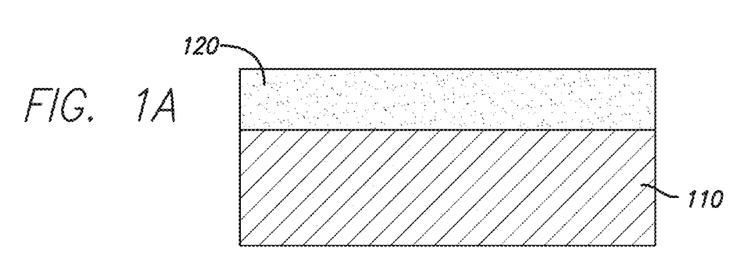
FIG. 1A shows an exemplary polymer layer on a planar substrate.

FIG. 1A shows a cross-sectional view of a planar substrate (110) coated with a polymer layer (120). By way of example and not of limitation, the planar substrate (110) as described in the present disclosure is made of silicon dioxide substrate, but the planar substrate (110) can be made of other materials such as quartz, fused silica, or sapphire. The planar substrate (110) can also be made of single element or compound semiconductors such as silicon, germanium, or gallium arsenide. In general, the planar substrate (110) can be of any material that does not fluoresce or otherwise generate large background signal in the spectral region of interest The polymer layer (120) comprises two or more chemically different polymer blocks that are chemically bonded together on each molecular chain but can microphase separate and form one or more periodic array of nanostructures (130) of FIG. 1B due to chemical incompatibility between the two or more blocks. The microphase separation is analogous to the separation of oil and water. The periodic array of nanostructures (130) formed from the polymer layer (120) can be substantially spherical, cylindrical, or lamellar. The polymer layer (120) can be a block copolymer. The polymer layer can specifically be made of polystyrene-poly(methyl methacrylate), polystyrene-polybutadiene-polystyrene, or other polymers.

Figure 1B:
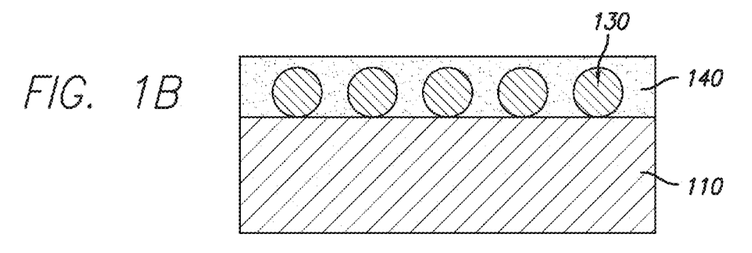
FIG. 1B shows an exemplary array of nanostructures in a polymer matrix on the planar substrate.

FIG. 1B shows a cross-sectional view of the polymer layer (120) of FIG. 1A on the planar substrate (110) after annealing. The annealing process heats the polymer layer (120) of FIG. 1A to a temperature high enough to allow the molecular chains to move and the blocks to microphase separate and form periodic nanostructures (130), which are thermodynamically favorable.

Figure 1C:
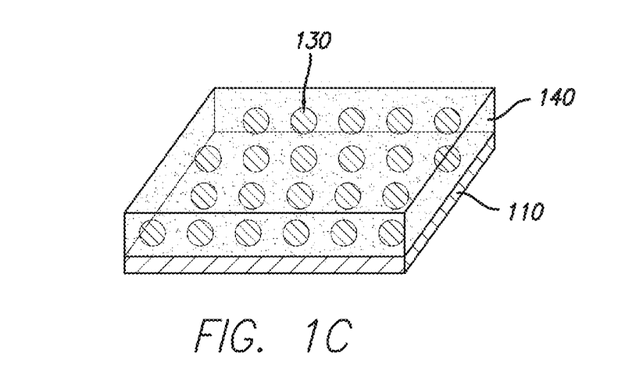
FIG. 1C shows a perspective view of the exemplary array of nanostructures in a polymer matrix on the planar substrate.

For example, FIG. 1C shows a first portion of the polymer layer (120) of FIG. 1A forming an array of nanostructures (130) with substantially spherical shape while a second portion of the polymer layer (120) of FIG. 1A forms a polymer matrix (140) surrounding the array of nanostructures (130). FIG. 1C shows a perspective view of the annealed polymer layer (120) of FIG. 1A after annealing whereby the microphase separation forms the array of nanostructures (130) and the polymer matrix (140).

Figure 1D:
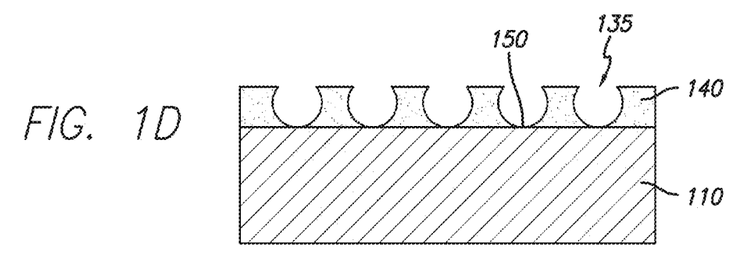
FIG. 1D shows an exemplary array of nanorecesses in a polymer matrix on the planar substrate.

FIG. 1D shows a cross-sectional view of the annealed polymer layer (120) on the planar substrate (110) where the array of substantially spherical nanostructures (130) has been removed. Removal can be done by reactive ion etch or other methods. After the array of nanostructures (130) has been removed, the polymer matrix (140) remains and surrounds an array of nanoscale recesses or nanorecesses (135).

The resulting array of nanorecesses (135) is highly uniform, and can cover areas as large as a whole wafer many inches in diameter (e.g., 4, 6 or 12 inches). Each of the nanorecesses (135) of the array of nanorecesses (135) can have an associated exposed portion of the planar substrate (150) below each of the removed nanostructures (130).

Figure 1E:
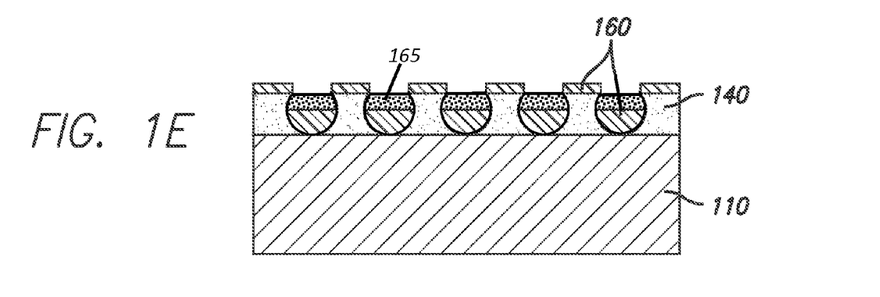
FIG. 1E shows an exemplary array of nanorecesses in a polymer matrix on the planar substrate covered by a first metal.

FIG. 1E shows a cross-sectional view of the array of nanorecesses (135) on the planar substrate (110) coated by a first metal (160). The first metal (160) can be silver, gold, aluminum, iridium platinum, palladium, copper or any other metal or metal alloy. The first metal (160) coats the top surface of the polymer matrix (140), and also the exposed portions of the planar substrate (150) below each of the removed nanostructures. The coating by the first metal (160) can be done by electrochemical deposition, electron beam evaporation (angled or orthogonal), physical sputtering, atomic layer deposition or other methods. The structure shown in FIG. 1E is an array of nanorecesses (135) suitable for SERS that can be referred to as nanodimples.

The array of nanorecesses (135) from FIG. 1E can be utilized as a SERS substrate fabricated with air covering and filling the nanorecesses (135). Other dielectric materials (165), such as silicon dioxide can be used to cover and fill the nanorecesses (135) to tune the array structure suitable for SERS.

Figure 1F:
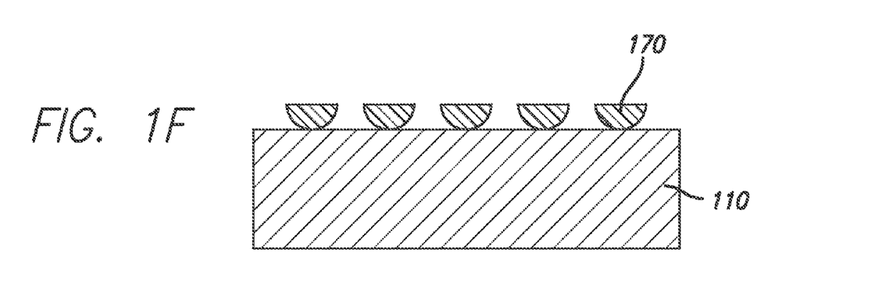
FIG. 1F shows an exemplary array of metal islands on the planar substrate.

FIG. 1F shows a cross-sectional view of the array of FIG. 1E after the polymer matrix (140) and the portion of the first metal (160) in FIG. 1E on the polymer matrix (140) have been removed. The remaining portion of the first metal (160) in FIG. 1E forms an array of metal islands (170) on the planar substrate (110). The removal of the polymer matrix (140) and the portion of the first metal (160) in FIG. 1E on top of the polymer matrix (140) can be accomplished by methods such as reactive ion etch, ion milling, or aqueous or solvent based wet removal methods.

Figure 1G:
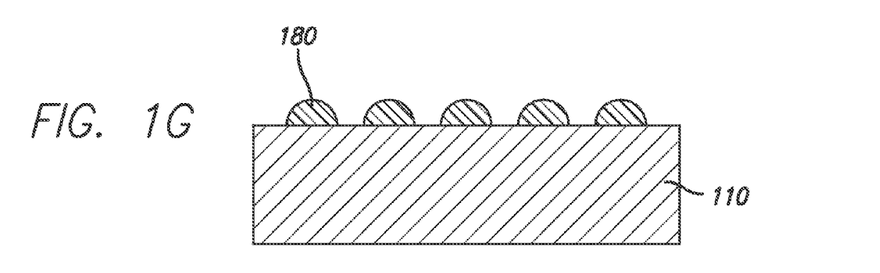
FIG. 1G shows an exemplary array of metal drops on the planar substrate.
Figure 1H:
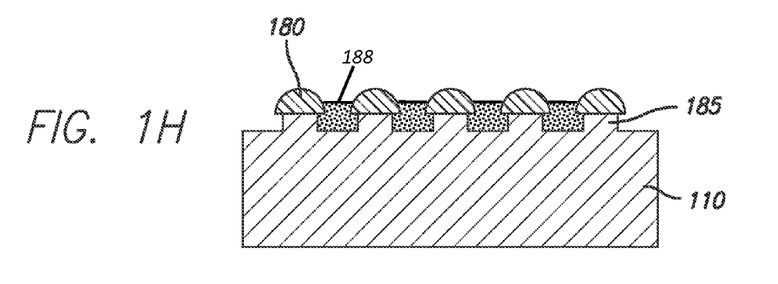
FIG. 1H shows an exemplary array of metal drops on an array of nanopillars on the planar substrate.

FIG. 1G shows a cross-sectional view of the array of metal islands (170) of FIG. 1F on the planar substrate (110) after annealing to reflow temperature, whereby the array of metal islands (170) of FIG. 1F now forms an array of metal drops (180) on the planar substrate (110). The metal drops (180) form a mask for a subsequent removal or etching process whereby portions of the planar substrate (110) not covered by the metal drops (180) are etched or removed. As a result of the etching or removing, an array of nanopillars (185) is formed under the array of metal drops (180) from the remaining planar substrate (110) as shown in FIG. 1H. In particular, FIG. 1H shows a cross-sectional view of the array of nanopillars (185) of FIG. 1H after the etching or removal process.

Figure 1I:
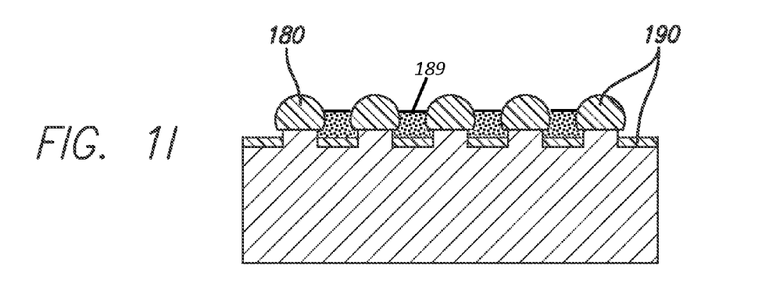
FIG. 1I shows an exemplary array of metal drops on an array of nanopillars on the planar substrate covered by a second metal.

FIG. 1I shows a cross-sectional view of the array nanopillars (185) of FIG. 1H after a coating of a second metal (190) which covers the metal drops (180) on top of each of the nanopillars and the exposed portions of the planar substrate. The second metal (190) can be silver, gold, aluminum, iridium platinum, palladium, copper or any other metal. The second metal (190) can be of the same material as the first metal (160) in FIG. 1E. The coating by the second metal (190) can be done by electrochemical deposition, electron beam deposition (angled or orthogonal), physical sputtering, atomic layer deposition, or other methods.

Figure 1J:
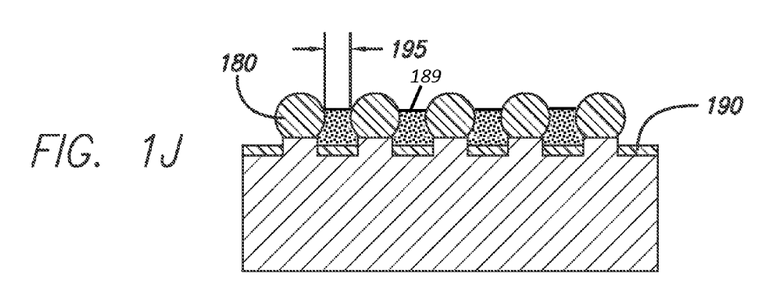
FIG. 1J shows an exemplary array of metal drops on an array of nanopillars on the planar substrate after a second anneal.

FIG. 1J shows a structure formed by the array of metal drop (180) covered nanopillars and the second metal (190) covered planar substrate (110) from FIG. 1H after a second annealing process. The array of metal drops (180) coated by the second metal (190) is heated again in the second annealing process to reflow whereby a shape change occurs in each metal drop (180) of the array of metal drops (180). The metal drops (180) have a gap width (195) of about 50 nm or less and preferably about 10 nm or less. The metal drops (180) can be substantially spherical in shape.

The array of metal drop (180) covered nanopillars (185) from FIGS. 1H-1I can be utilized as a SERS substrate as fabricated with air covering and filling an area between the metal drops (180) and between the nanopillars (185) in FIG. 1H. Other dielectric materials (188, 189), such as silicon dioxide, can be used to cover and fill in between the metal drops (180) and in between the nanopillars (185) to tune the array structure suitable for SERS.

FIGS. 1A-1J show an embodiment of the steps of fabricating an array structure suitable for SERS in accordance with the disclosure. The person skilled in the art will understand that the number of such steps is only indicative and that the process can occur in more or fewer steps according to the various embodiments. For example, the metal drops (180) can be formed from a single metal layer rather than a first metal (160) and a second metal (190).

FIGS. 2A-2I show another embodiment of the steps of fabricating an array structure suitable for SERS in accordance with the disclosure.

Figure 2A:
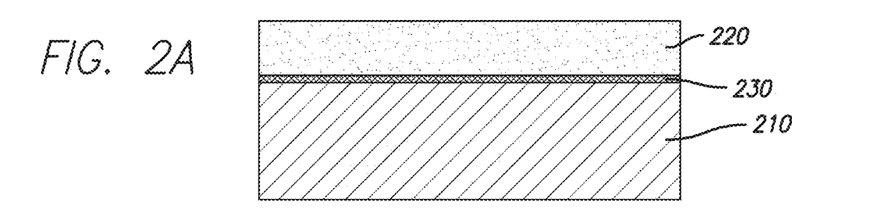
FIG. 2A shows an exemplary photoresist layer on an exemplary antireflective layer on a planar substrate.

FIG. 2A shows a planar substrate (210) coated with an antireflective layer (230), and the antireflective layer (230) is coated with a photoresist layer (220). The antireflective layer (230) is an optional layer which serves to improve the effective resolution of the photoresist layer (220) interaction with the light source by reducing or removing the reflection from the substrate (210). For some non-reflective substrates or larger dimension process, the antireflective layer (230) may be optional. In an embodiment of the present disclosure, an average 0.45 µm thick photoresist layer (220) is used. More details regarding the planar substrate (210) are disclosed in the description of FIG. 1A.

Figure 2B:
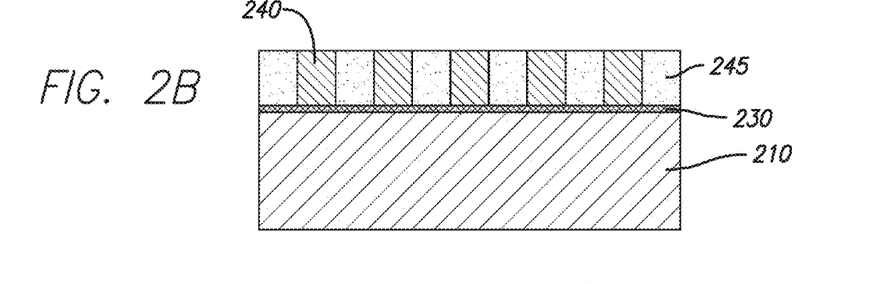
FIG. 2B shows an exemplary photoresist layer on an exemplary antireflective layer on a planar substrate after exposure with laser interference lithography.
Figure 3:
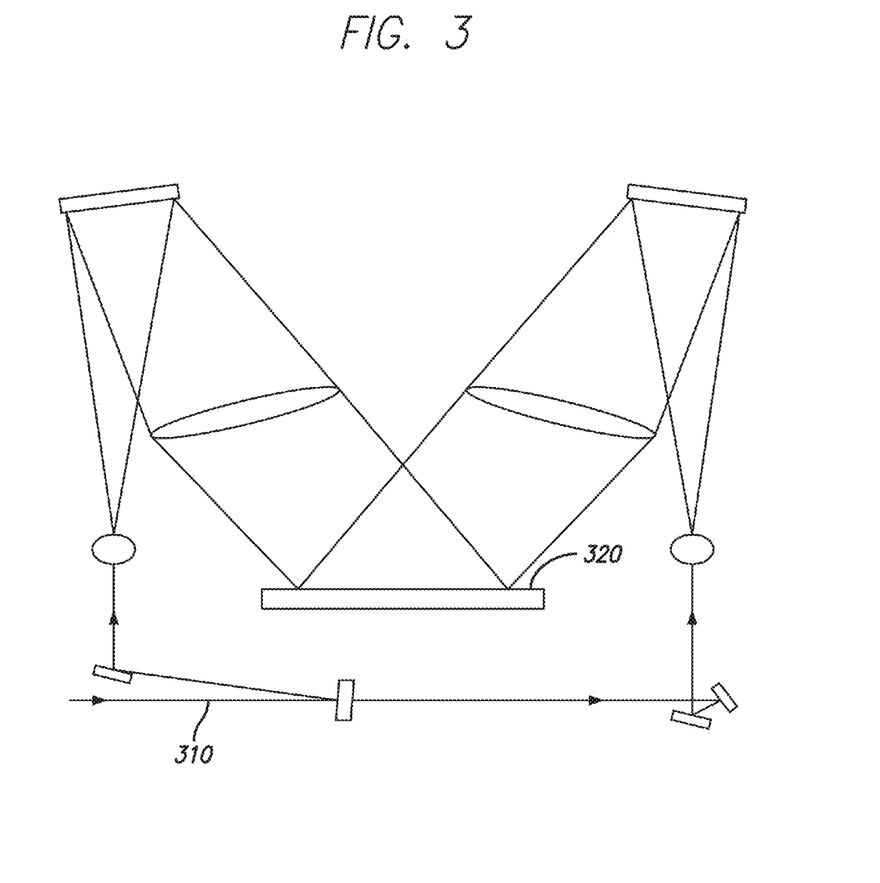
FIG. 3 shows an exemplary laser interference lithography system.

FIG. 2B shows the photoresist layer (220) in FIG. 2A on the antireflective layer (230) on the planar substrate (210) after the photoresist layer (220) in FIG. 2A has been exposed with a spatial interference pattern (320) formed by laser light (310), shown in FIG. 3 in a process known as laser interference lithography [Fernandez et al., 1997 *J. Vac. Sci. Technol. B* 15(3) 729-735].

Referring now to FIG. 3, laser interference lithography is described graphically. Laser interference lithography can be conducted by splitting the laser light (310) from a single source into two beams. Each of the two beams is spread with optical components and then recombined to create a two dimensional spatial interference pattern (320) by the constructive and destructive interference of the beams. The constructive interference forms bright regions where the two beams are added, and the destructive interference forms dark regions where the two beams cancel one another. The spatial interference pattern (320) is then used to expose the photoresist layer (220) in FIG. 2A. Although a single source of laser light (310) is shown here, two separate sources can be used. In an embodiment of the present disclosure, 413 nm wavelength laser interference illuminated with a dose of ~40 mJ/cm$^2$ is used [Gartia et al., 2010 Nanotechnology 21 395701-395709].

Returning to FIG. 2B, the photoresist layer (220) in FIG. 2A undergoing a chemical change upon exposure by the spatial interference pattern (320) is shown. The exposed portions of the photoresist layer (220) in FIG. 2A undergo a chemical change which causes the exposed portions to become either soluble or insoluble in the developer solution as compared to the unexposed portion depending on the tone of the resist (e.g., positive or negative). Therefore, the exposure converts the photoresist layer (220) in FIG. 2A into two portions: the first portion is an array of photoresist islands (240) and the second portion is a photoresist matrix (245) which surrounds the array of photoresist islands (240). One portion is typically more soluble in the developing solution than the other. The photoresist islands (240) are typically cylindrical in shape.

Figure 2C:
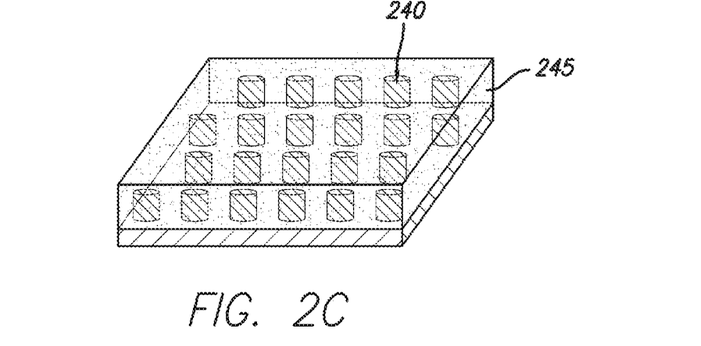
FIG. 2C shows a perspective view of the exemplary photoresist layer on an exemplary antireflective layer on a planar substrate after exposure with laser interference lithography.

FIG. 2C shows a perspective view of the exposed photoresist layer (220) in FIG. 2A showing the array of photoresist islands (240) in a photoresist matrix (245). In an embodiment of the present disclosure, the photoresist islands (240) are cylindrical in shape and are individually 150 nm in diameter and 350 nm in pitch [Gartia et al., 2010 Nanotechnology 21 395701-395709]. The pitch of the photoresist islands (240) (e.g., distance from the center of the photoresist island (240) to the center of the next photoresist island (240)) can be changed or tuned by utilizing a different type of laser source. Also, the size of each of the photoresist islands (240) can be adjusted by selecting or developing a photoresist with a non-linear response to light exposure.

Figure 2D:
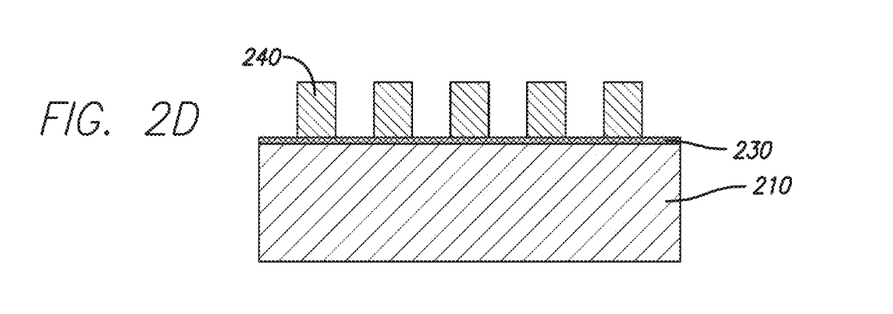
FIG. 2D shows an exemplary array of photoresist islands on a planar substrate after exposure with laser interference lithography and development.

FIG. 2D shows the array of photoresist islands (240) remaining after the exposed photoresist layer (220) in FIG. 2A is developed by applying a development solution which dissolves the photoresist matrix (245) selectively.

Figure 2E:
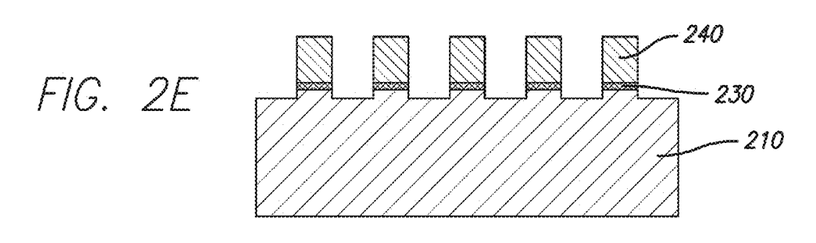
FIG. 2E shows an exemplary array of photoresist islands on a planar substrate after exposure with laser interference lithography, development, and some removal of the exposed portions of the planar substrate.

FIG. 2E shows portions of the planar substrate (210) partially removed by a removal process such as ion milling, reactive ion etch, or wet etch. The portions of the planar substrate (210) covered by the array of photoresist islands (240) are protected while the exposed portions of the planar substrate (210) are removed. In an embodiment of the present disclosure, the removal of the exposed portions of the planar substrate (210) is done by an ion milling deep reactive ion etch by a highly directional Bosch process [Garda et al., 2010 Nanotechnology 21 395701-395709].

Figure 2F:
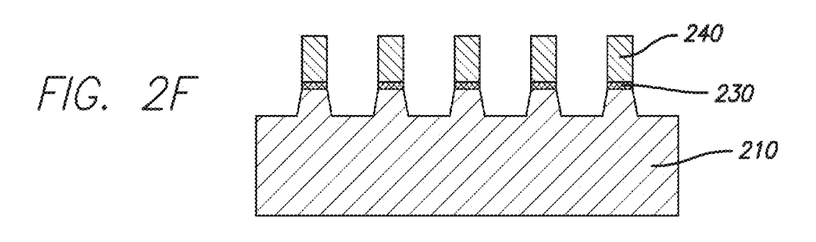
FIG. 2F shows an exemplary array of photoresist islands on a planar substrate after exposure with laser interference lithography, development, and additional removal of the exposed portions of the planar substrate.
Figure 2G:
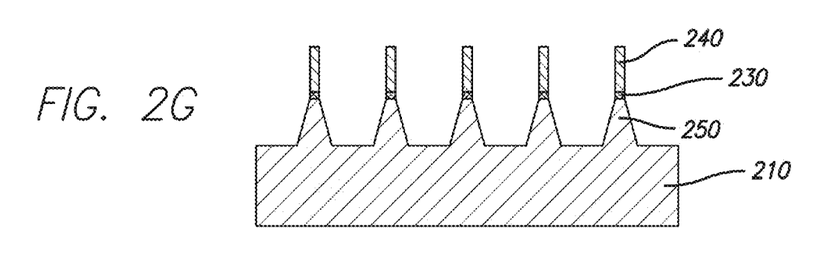
FIG. 2G shows an exemplary array of photoresist islands on a planar substrate after exposure with laser interference lithography, development, and after completion of the removal of the exposed portions of the planar substrate.

FIGS. 2E-2G show the progression of the removal process for the planar substrate (210) from FIG. 2E to FIG. 2F to FIG. 2G where each island of the array of photoresist islands (240) is also removed or etched laterally or horizontally as the removal or etching process for the planar substrate (210) progresses. The lateral removal rate for the photoresist islands (240) may be much slower than the removal rate of the exposed portions of the planar substrate (210). The result of this particular feature of the removal process for the planar substrate (210) is the formation of an array of tapered nanopillars (250) having a conical form that is tapered thinner at the tip and wider at the base whereby the base is on the planar substrate (210).

The applicants note that other removal processes for the planar substrate (210) can be used. In case the photoresist islands (240) are not etched laterally or horizontally during the removal process for the planar substrate (210), straight nanopillars rather than tapered nanopillars would result. Arrays of straight nanopillars can also be covered by metal and be utilized as SERS structures.

By way of example and not of limitation, in an embodiment of the present disclosure, the tapered nanopillars (250) are 500 nm in height and made of silicon dioxide material [Garda et al., 2010 Nanotechnology 21 395701-395709]. As previously noted in the description of FIG. 2C in the present disclosure, the photoresist islands (240), and thus the tapered nanopillars (250) can individually be approximately 150 nm in diameter at the base which is on the planar substrate (210) and 350 nm in pitch. Furthermore, the applicants note that for the tapered nanopillars (250) and other array structures suitable for SERS, higher periodicity is desirable in creating a better enhancement factor with more hot spots per area.

Figure 2H:
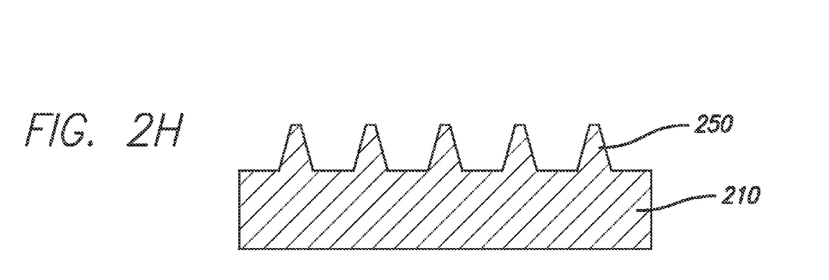
FIG. 2H shows an exemplary array of tapered nanopillars on a planar substrate after the remaining photoresist islands are removed.

FIG. 2H shows the array of tapered nanopillars (250) after the remaining photoresist islands (240) in FIG. 2G and the antireflective layer (230) in FIG. 2G are removed. The tapered nanopillars (250) may have sharp tips on top. The resulting array of tapered nanopillars (250) from this process is highly uniform, and can cover areas as large as a whole wafer that is many inches in diameter (e.g., 4, 6 or 12 inches). In an embodiment of the present disclosure, the resulting array covers a whole 4-inch wafer [Garda et al., 2010 Nanotechnology 21 395701-395709].

Figure 2I:
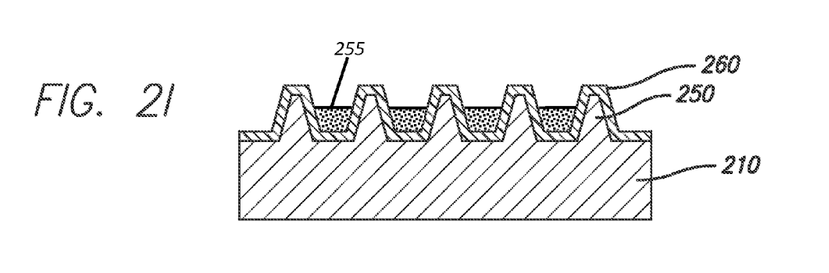
FIG. 2I shows an exemplary array of tapered nanopillars on a planar substrate coated with a metal layer.

FIG. 2I shows the array of tapered nanopillars (250) on the planar substrate (210) covered by a metal layer (260). The metal layer (260) covers both the array of tapered nanopillars (250) and the exposed portions of the planar substrate (210). The metal layer (260) can be silver, gold, aluminum, iridium platinum, palladium, copper or any other metal. The covering by the metal layer (260) can be done by electrochemical deposition, electron beam deposition (angled or orthogonal), physical sputtering, atomic layer deposition, or other methods. In an embodiment of the present disclosure, the metal layer (260) is an 80 nm thick film of silver deposited by e-beam evaporation [Garda et al., 2010 Nanotechnology 21 395701-395709].

The array of tapered nanopillars (250) can be utilized as SERS substrate fabricated with air filling in between the tapered nanopillars (250). Other dielectric materials (255), such as silicon dioxide can be used to cover and fill in between the tapered nanopillars (250) to tune the array structure suitable for SERS. The person skilled in the art will, again, understand that the number of steps shown in FIG. 2A-2I is only indicative and that the process can occur in more or fewer steps according to the various embodiments.

Figure 6:
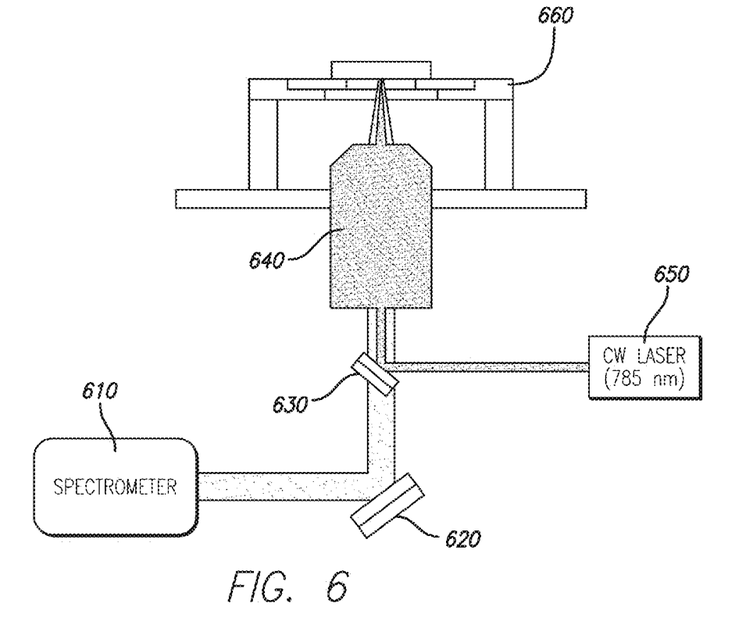
FIG. 6 shows an exemplary far field scanning confocal Raman microspectroscopy system capable of SERS measurements.
Figure 7A:
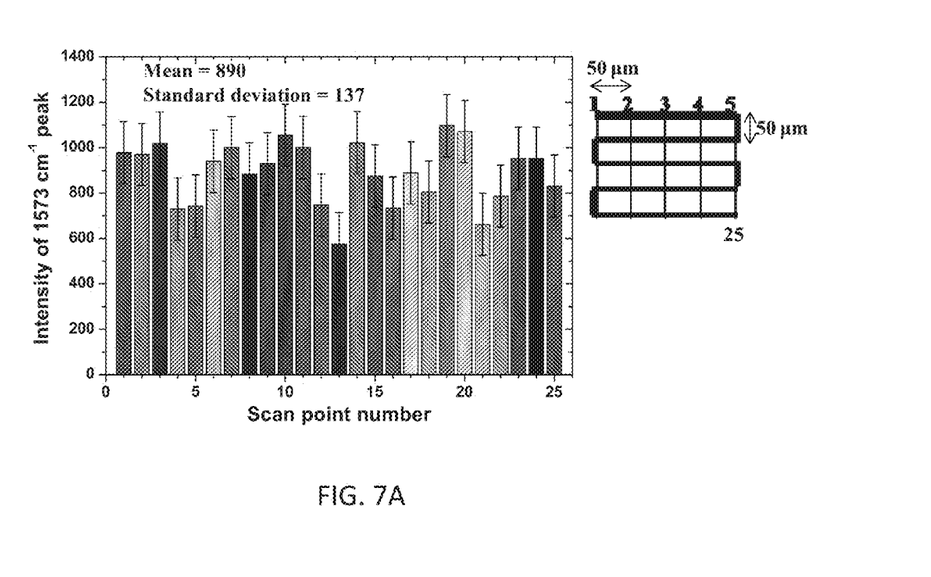
FIGS. 7A-7B show an exemplary SERS measurement showing enhancement factor and uniformity.
Figure 7B:
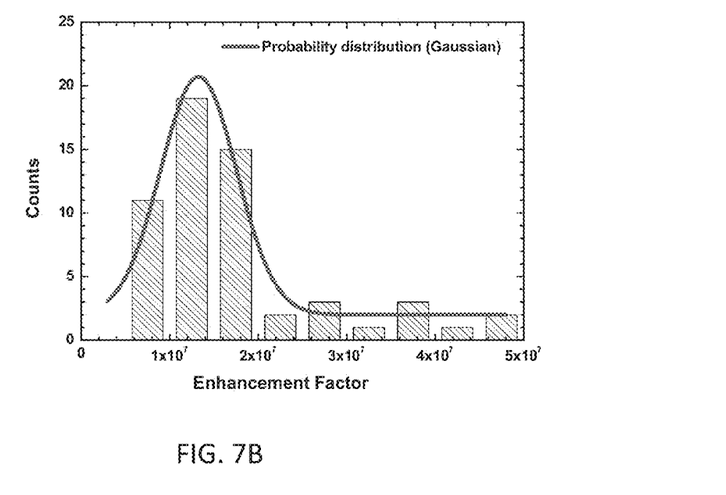

FIG. 6 shows an example of a far field scanning confocal Raman microspectroscopy system capable of far field SERS measurements to evaluate the performance of the array structure suitable for SERS. The far field scanning confocal Raman microspectroscopy system shown in FIG. 6 comprises a spectrometer (610), a mirror (620), a dichroic optical element (630), a collection lens (640), a laser (650), and a sample platform (660). In one embodiment of this disclosure, an average enhancement factor of well into the $10^7$ range (see FIG. 7B) is measured for the array of tapered nanopillar (250) in FIG. 2H as SERS substrate, with a good repeatability over a 250 μm square region as shown in FIG. 7A [Garda et al., 2010 Nanotechnology 21 395701-395709].

In the present disclosure, the applicants disclose two additional methods of characterizing the array structure suitable for SERS besides the far field scanning confocal Raman microspectroscopy. First, near field scanning optical microscopy (NSOM) is a microscopic technique for nanostructure investigation that breaks the far field resolution limit by directly detecting the near field emission or scattering. This is done by placing the detector very close (where the distance is far less than the wavelength, typically a few nanometers) to the specimen surface. This allows for surface optical inspection with high spatial, spectral and temporal resolving power. By scanning the NSOM tip, the two dimensional Rayleigh scattering light tomograph can be obtained which can be directly compared to simulation results. The light enhancement factor can also be acquired directly. Besides the near field Rayleigh scattering measurement, the NSOM system can be coupled with a Raman spectroscopy system to measure the SERS spectra in the near field.

Another potentially important method for characterizing the array structures suitable for SERS described in the present disclosure is the use of local quantum-confined Stark effect. Although the NSOM can give the scattering light profile at the SERS hot spot with typically tens of nanometers in resolution, it is still important to measure the local electric field with an even higher spatial resolution as the size of the SERS hot spot is usually smaller than 10 nanometers. A characterization technique to obtain the accurate electric field information with potentially nanometer spatial resolution is to place semiconductor quantum dots (QD) or artificial fluorophore molecules in the hot spot, and measure the QD bandgap change when applying optical excitation to the SERS hot spot. The asymmetrical charge-carrier distribution function in semiconductor materials favors holes in the direction of the applied electric field and electrons in the opposite direction, which leads to a tilted band diagram. In this case the applied field leads to a reduction in the effective bandgap through the Stark effect.

By exploiting quantum-size effects in small scale structures, the reduction in the effective bandgap can be magnified in quantum dots, or quantum wells through the quantum-confined Stark effect (QCSE). The bandgap condition of QD can be examined optically by photoluminescence measurement and/or fluorescence spectroscopy. The real local electric field amplitude or intensity can be calculated from the measurements with good confidence.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually, even if the citation refers to only the first page of the reference.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A structure comprising:
   a planar substrate;
   an array of nanopillars on the planar substrate, the array of nanopillars substantially perpendicular to the planar substrate and having a substantially cylindrical shape;
   a metal drop comprising a first metal and a second metal, the metal drop having a substantially spherical shape, the second metal of the metal drop uniformly covering the first metal of the metal drop on each nanopillar of the array of nanopillars, wherein
   the second metal further covers a surface of the planar substrate with a layer having a uniform thickness; and
   a dielectric material covering and filling a region between adjacent metal drops and between adjacent nanopillars.

2. The structure of claim 1, wherein the planar substrate and the array of nanopillars are selected from the group consisting of: silicon dioxide, fused silica, sapphire, silicon, and compound semiconductors.

3. The structure of claim 1, wherein the second metal is selected from the group consisting of: silver, gold, aluminum, iridium platinum, palladium, and copper.

4. The structure of claim 1, wherein size, gap width and height of the array of the nanopillars and size, gap width and height of the metal drops on the array of the nanopillars are configured to enable surface enhancement of Raman scattering (SERS).

5. The structure of claim 1, wherein a gap width between the metal drops on the array of nanopillars is less than approximately 50 nm.

6. The structure of claim 1, wherein a gap width between the metal drops on the array of nanopillars is less than approximately 10 nm.

7. The structure of claim 1, the structure being a SERS substrate.

8. A method of measuring a light enhancement factor for an array structure in surface enhanced Raman scattering (SERS), the method comprising:
   providing the structure according to claim 1;
   contacting a plurality of molecules with the structure, the plurality of molecules being on the metal drop and on the second metal; and
   measuring a near field scattering intensity from the structure with a near field scanning optical microscope, thus measuring the light enhancement factor for the structure in surface enhanced Raman scattering (SERS).

9. The method of claim 8, the structure being a SERS substrate.

10. The structure of claim 1, wherein the dielectric material is silicon dioxide.

11. A structure comprising:
a planar substrate;
an array of nanorecesses in the planar substrate;
a first metal covering the planar substrate and the array of nanorecesses, the first metal covering the planar substrate with a layer having a uniform thickness; and
a dielectric material covering and filling the nanorecesses.

12. The structure of claim 11, wherein the planar substrate is selected from the group consisting of: silicon dioxide, fused silica, sapphire, silicon, and compound semiconductors.

13. The structure of claim 11, wherein the first metal is selected from the group consisting of: silver, gold, aluminum, iridium platinum, palladium, and copper.

14. The structure of claim 11, wherein size, spacing, and depth of the array of the nanorecesses and depth of the first metal covering at least a portion of each nanorecess is configured to enable surface enhancement of Raman scattering (SERS).

15. The structure of claim 11, the structure being a SERS substrate.

16. The structure of claim 11, wherein the nanorecesses in the planar substrate have a spherical shape.

17. The structure of claim 11, wherein the dielectric material is silicon dioxide.

18. A structure comprising:
a planar substrate;
an array of tapered nanopillars on the planar substrate, wherein each tapered nanopillar of the array of tapered nanopillars is substantially perpendicular to the planar substrate and have a substantially conical shape, the conical shape being wider on a side connected with the planar substrate and tapered on a side opposite the planar substrate;
a metal layer covering a surface of the planar substrate and covering each tapered nanopillar of the array of tapered nanopillars, said metal layer covering the surface of the planar substrate with uniform thickness; and
a dielectric material covering and filling in between the tapered nanopillars.

19. The structure of claim 18, wherein the planar substrate and the array of tapered nanopillars are selected from the group consisting of: silicon dioxide, fused silica, sapphire, silicon, and compound semiconductors.

20. The structure of claim 18, wherein the metal layer is selected from the group consisting of: silver, gold, aluminum, iridium platinum, palladium, and copper.

21. The structure of claim 18, wherein size, pitch, and height of the array of tapered nanopillar and thickness of the metal layer covering at least a portion of each tapered nanopillar is configured to enable surface enhancement of Raman scattering (SERS).

22. The structure of claim 18, the structure being a SERS substrate.

23. The structure of claim 18, wherein the tapered nanopillars have sharp tips on top.

24. A structure comprising:
a planar substrate;
an array of straight nanopillars on the planar substrate, wherein each straight nanopillar of the array of straight nanopillars is substantially perpendicular to the planar substrate and has a substantially cylindrical shape;
a metal layer covering a surface of the planar substrate and covering each straight nanopillar of the array of straight nanopillars, said metal layer covering the surface of the planar substrate with uniform thickness; and
a dielectric material covering and filling in between the straight nanopillars.

25. The structure of claim 24, the structure being a SERS substrate.

26. The structure of claim 24, wherein the metal layer is an 80 nm thick film of silver deposited by e-beam evaporation.

27. The structure of claim 24, wherein the nanopillars are 500 nm in height and made of silicon dioxide material.

28. The structure of claim 24, wherein each nanopillar is 150 nm in diameter at the base adjacent to the substrate and 350 nm in pitch.

29. A structure comprising:
a planar substrate;
an array of nanopillars on the planar substrate, the array of nanopillars substantially perpendicular to the planar substrate and having a substantially cylindrical shape; and
a metal drop comprising a metal, the metal drop having a substantially spherical shape formed on each nanopillar of the array of nanopillars,
wherein the metal further covers a surface of the planar substrate with a layer having a uniform thickness, and
wherein the lateral area of each nanopillar is partially covered by the metal.

30. The structure of claim 29, a gap width between the metal drops on the array of nanopillars is less than 10 nm.

* * * * *